(12) United States Patent
Hayashi et al.

(10) Patent No.: US 7,687,085 B2
(45) Date of Patent: Mar. 30, 2010

(54) ANTI-OBESTIC COMPOSITION

(75) Inventors: Syuichi Hayashi, Osaka (JP); Kazuya Nakagawa, Osaka (JP); Keiichiro Sugimoto, Osaka (JP)

(73) Assignee: Nagaoka Perfumery Co., Ltd, Osaka (JP)

( * ) Notice: Subject to any disclaimer, the term of this patent is extended or adjusted under 35 U.S.C. 154(b) by 556 days.

(21) Appl. No.: 11/593,554

(22) Filed: Nov. 7, 2006

(65) Prior Publication Data

US 2007/0054000 A1 Mar. 8, 2007

Related U.S. Application Data

(62) Division of application No. 10/263,197, filed on Oct. 3, 2002, now Pat. No. 7,150,889, which is a division of application No. 09/761,652, filed on Jan. 18, 2001, now abandoned.

(30) Foreign Application Priority Data

Jan. 18, 2000 (JP) ................................. 2000-9519

(51) Int. Cl.
*A61K 36/61* (2006.01)
(52) U.S. Cl. ..................................................... 424/742
(58) Field of Classification Search ........................ None
See application file for complete search history.

(56) References Cited

U.S. PATENT DOCUMENTS

| 5,578,338 | A | 11/1996 | Shimabukuro |
| 5,698,199 | A | 12/1997 | Mori et al. |
| 6,475,530 | B1 | 11/2002 | Kuhrts |

FOREIGN PATENT DOCUMENTS

| JP | 3-228664 | 10/1991 |
| JP | 5-252897 | 10/1993 |
| JP | 6-199677 | 7/1994 |
| JP | 6-227996 | 8/1994 |
| JP | 9-2963 | 1/1997 |
| JP | 9-2966 | 1/1997 |
| JP | 9-176019 | 7/1997 |
| JP | 9-291039 | 11/1997 |
| JP | 2001-163795 | 6/2001 |

OTHER PUBLICATIONS

Patent Abstracts of Japan 06-19967, Jul. 19, 1994.
Patent Abstracts of Japan 09-291039, Nov. 11, 1997.
Patent Abstracts of Japan 09-176019, Jul. 8, 1997.
Patent Abstracts of Japan 09-002963, Jan. 7, 1997.
Patent Abstracts of Japan 06-227996, Aug. 16, 1994.
Patent Abstracts of Japan 05-252897, May 10, 1993.
Patent Abstracts of Japan 09-002966, Jan. 7, 1997.
Patent Abstracts of Japan 03228664 A, Oct. 9, 1991.
Allison M. Gray et al., "Biochemical and Molecular Roles of Nutients, vol. 128, No. 12, p. 2319-2323, 1998 "Studies in vivo, p. 2321, left column.
The Merck Manual, Sixteenth Edition, Ch. 83, pp. 1039-1048, Pub Date 1992.
Hingston, "Activity of polyphenolic constituents of leaves of Eucalyptus and other species in complexing and dissolving iron oxide," Abstract Caplus 1964:11268 [Australian J. Soil Res (1963)1(1) pp. 63-73].
Hillis et al "Influence of extractives on eucalypt pulping and papermaking" Abstract Caplus 1960:3982 [Appita (1959) 13, pp. 74-83].
Me et al "Tanis from Bendo Eucalyptus" Abstract Biosis [Acta Botanica Sinica 1988 vol. 30, No. 5 pp. 534-538.
Glick "Modes of Action of Gallic Acid in Supressing Food Intake of Rats" J. Nutr. (1981) 111, No. 11, pp. 1910-1916.

*Primary Examiner*—Herbert J. Lilling
(74) *Attorney, Agent, or Firm*—Sughrue Mion, PLLC

(57) ABSTRACT

The composition of the present invention comprises (1) a biologically effective amount of an extract of a plant of the genus *Eucalyptus* as an active ingredient, and (2) a biologically acceptable carrier or diluent, and is effective for inhibiting or preventing obesity (increase in weight), lipid storage disease, hyperlipemia, arteriosclerosis, or thrombosis, and is also effective for inhibiting or reducing an amount of triglyceride or an amount of cholesterol in blood. Therefore, the composition of the present invention is used in the form of drugs, food products, food additives, animal feeds, and additives for animal feeds.

1 Claim, 10 Drawing Sheets

Weight of adipose tissue stored in the vicinity of epididymis per kg of weight

US 7,687,085 B2

ANTI-OBESTIC COMPOSITION

This is a divisional of application Ser. No. 10/263,197 filed Oct. 3, 2002, now U.S. Pat. No. 7,150,889 which is a divisional of application Ser. No. 09/761,652, filed Jan. 18, 2001, now abandoned. The entire disclosures of the prior applications, application Ser. Nos. 09/761,652 and 10/263,197 are hereby incorporated by reference.

FIELD OF THE INVENTION

The present invention relates to an anti-obestic composition, a lipid storage inhibitor composition, an anti-lipemic composition, an anti-arteriosclerotic composition, an anti-thrombotic composition, a composition for reducing a concentration of cholesterol in blood and a composition for reducing a concentration of triglyceride in blood, each of which contains an extract of a plant of the genus *Eucalyptus* as an active ingredient, a method of inhibiting or preventing obesity (increase in weight) lipid storage disease, hyperlipemia, arteriosclerosis and thrombosis, and a method of inhibiting or reducing an amount of triglyceride in blood and an amount of cholesterol in blood.

BACKGROUND OF THE INVENTION

Obesity is one of risk factors of various diseases such as arteriosclerosis. Therefore, it is strongly required to inhibit, ameliorate or prevent obesity. Obesity is a state where excess lipid is stored in the body. One of causes for lipid storage in the body includes, for example, excess ingestion of carbohydrate. When ingested in the body, carbohydrate contained in food products and beverages is generally digested by a digestive enzyme to exclusively form a monosaccharide, which is absorbed into the body through the enteric canal. The monosaccharide is converted into lipid in the lipid cells to form an adipose tissue. It is considered that various pathologies are caused by intraperitoneal storage of visceral lipid among these adipose tissues.

In case a large amount of saccharides such as fructose are ingested in the form of sucrose, portion of the saccharides promotes the synthesis of fatty acid in the liver and also enhaces the esterification of fatty acid. As a result, a large amount of triglyceride (triacyl glycerol, neutral lipid) is produced.

The liver converts triglyceride into a very low-density lipoprotein (VLDL) and secretes it in blood serum. In that case, when a large amount of triglyceride is produced, an ability capable of producing lipoprotein of the liver does not follow so that triglyceride is stored in the liver and fatty liver progresses, thus entering into cirrhosis soon.

An increase in secretion of VLDL causes hyperlipemia. Hyperlipemia is also caused by a reduction in insulin sensitivity (insulin resistance) due to excess ingestion of carbohydrate and deteriorates disease conditions. An increase in VLDL concentration in blood is also a major cause for arteriosclerosis. Arteriosclerosis causes thrombosis and is also one of factors for various circulatory system diseases such as cerebral infarction and cardiac infraction.

As described above, excess ingestion of saccharides causes obesity, thus causing various diseases. Therefore, there has hitherto been developed an anti-obestic agent, which can inhibit, ameliorate or prevent obesity by inhibiting any pathway leading to obesity.

Typical anti-obestic agent includes a carbohydrate digestive enzyme inhibitor, and an α-glucosidase inhibitor, for example, "Acarbose" (manufactured by Bayer Yakuhin, LTD.) has widely been used as a drug.

However, since a conventional anti-obestic agent is a chemically synthesized product, users feel uneasy in view of safety on administration. It could not sufficiently respond to requirements for inhibition or amelioration of obesity in a dairy life. It is particularly advantageous for inhibition, amelioration and prevention of obesity if an anti-obestic action can be imparted to food products and beverages, which are ordinarily ingested.

Therefore, various anti-obestic agents derived from natural substances such as plant have been suggested. For example, diet food products and beverages, containing an extract of Gymnema Indorum as a plant native to India is described in Unexamined Patent Publication (Kokai) No. Hei 5-252897. A weight control agent containing an oolong tea saponin and an oolong tea fiber is described in Unexamined Patent Publication (Kokai) No. Hei 9-227996. A carbohydrate digestive enzyme inhibitor containing an extract of Ephedra Herb used as a Chinese herbal remedy is described in Unexamined Patent Publication (Kokai) No. Hei 9-2963. An anti-obestic agent containing a seed coat extract of Tamarindus indica L. of the legminous family as an active ingredient is described in Unexamined Patent Publication (Kokai) No. Hei 9-291039.

However, an anti-obestic agent having a safe and higher anti-obestic action has been required. Furthermore, there has also been required an active ingredient derived from natural substances, which is also superior in action of inhibiting lipid storage, action of reducing a concentration of triglyceride and action of reducing a concentration of cholesterol in blood.

SUMMARY OF THE INVENTION

A main object of the present invention is to provide an anti-obestic composition having high safety and a high anti-obestic action, and a method of inhibiting or preventing obesity.

Another object of the present invention is to provide a lipid storage inhibitor composition, an anti-lipemic composition, an anti-arteriosclerotic composition, an anti-thrombotic composition, a composition for reducing a concentration of cholesterol in blood and a composition for reducing a concentration of triglyceride in blood, each of which has high safety and a high action of inhibiting lipid storage, a high anti-lipemic action, a high anti-arteriosclerotic action, a high action of reducing a concentration of triglyceride and a high action of reducing a concentration of cholesterol in blood, a method of inhibiting or preventing lipid storage disease, hyperlipemia, arteriosclerosis and thrombosis, and a method of inhibiting or reducing an amount of triglyceride and an amount of cholesterol in blood.

The present inventors have intensively studied to accomplish the objects described above and found a new fact that an extract of a plant of the genus *Eucalyptus* has an excellent action of inhibiting an increase in weight.

That is, the present invention provides an anti-obestic composition comprising:

(1) a biologically effective amount of an extract of a plant of the genus *Eucalyptus* (hereinafter referred merely to as "*Eucalyptus* extract") as an active ingredient, and (2) a biologically acceptable carrier or diluent.

Furthermore, the *Eucalyptus* extract in the present invention is effective for inhibition, amelioration or prevention of various diseases such as hyperlipemia, thrombosis and hypercholesterolemia, and is also effective for inhibition of an increase or reduction of an amount of triglyceride or an amount of cholesterol in blood, because it has an action of inhibiting lipid storage, an action of reducing a concentration of triglyceride and an action of reducing a concentration of cholesterol in blood. Accordingly, the present invention also provides a lipid storage inhibitor composition, an anti-lipemic composition, an anti-arteriosclerotic composition, an anti-thrombotic composition, a composition for reducing a concentration of cholesterol in blood and a composition for reducing a concentration of triglyceride in blood, each of which comprises both components (1) and (2) described above.

It is considered the *Eucalyptus* extract has an action of inhibiting an increase in weight, an action of inhibiting lipid storage, an action of reducing a concentration of triglyceride and an action of reducing a concentration of cholesterol in blood because of an action of inhibiting an activity of a digestive enzyme for saccharides, an action of inhibiting absorption of monosaccharide at the enteric canal and an action of inhibiting biosynthesis of lipid at the liver. The *Eucalyptus* extract in the present invention is particularly effective for inhibition, amelioration or prevention of various diseases caused by ingestion of sucrose (sugar) or analogues thereof, for example, obesity, lipid storage disease, hyperlipemia, thrombosis and hypercholesterolemia.

Accordingly, the present invention provides a method of inhibiting or preventing obesity, lipid storage disease, hyperlipemia, arteriosclerosis, thrombosis, an amount of triglyceride and an amount of cholesterol in blood, which comprises administering or ingesting a composition comprising both components (1) and (2) described above.

The *Eucalyptus* extract is a substance derived from natural substances and therefore has high safety. Therefore, it can be incorporated into food products (food products and beverages), food additives, animal feeds, and additives for animal feeds, in addition to drugs.

The other objects and advantages of the present invention will become apparent from the following description.

DETAILED DESCRIPTION OF THE INVENTION

Figure 1:
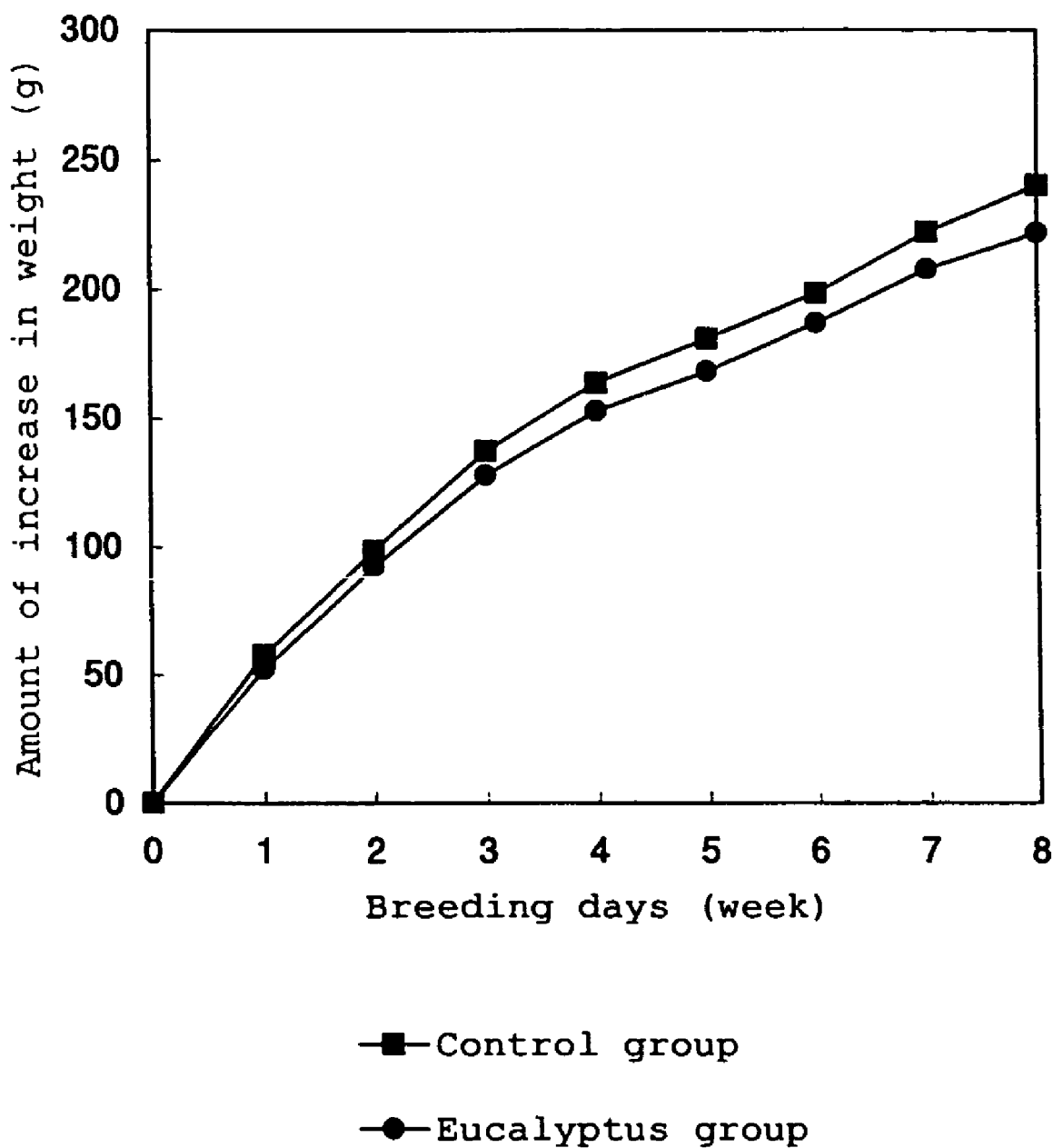
FIG. 1 is a graph showing an action of inhibiting an increase in weight in Test Example 1.

Examples of the plant of the genus *Eucalyptus* used in the present invention include *Eucalyptus globulus*, *Eucalyptus robusta*, *Eucalyptus mellidora*, *Eucalyptus cornuta*, *Eucalyptus beyeri*, *Eucalyptus deglupta*, *Eucalyptus dealbata*, *Eucalyptus microcorys*, *Eucalyptus citriodora*, *Eucalyptus paniculata*, *Eucalyptus umbra*, *Eucalyptus crebra*, *Eucalyptus albens*, *Eucalyptus tereticornis*, *Eucalyptus botryoides*, *Eucalyptus deanei*, *Eucalyptus ovata*, *Eucalyptus maculata*, *Eucalyptus piluaris*, *Eucalyptus piperita*, *Eucalyptus propinqua*, *Eucalyptus colassea*, *Eucalyptus exerta*, *Eucalyptus longifolia*, *Eucalyptus resinifera*, *Eucalyptus sideroxylon*, *Eucalyptus acmenioides*, *Eucalyptus gomphocephala*, *Eucalyptus punctana*, *Eucalyptus smithii*, *Eucalyptus rostrata*, *Eucalyptus viminalis*, and *Eucalyptus purvelulenta*, *Eucalyptus globulus* and *Eucalyptus robusta* are preferable. The section to be extracted in the plant of the genus *Eucalyptus* is not specifically limited and includes, for example, leaf, seed, trunk, and root. Leaf is particularly preferable.

A treatment for extraction from the plant of the genus *Eucalyptus* is conducted in the following procedure. First, a plant as a raw material, preferably leaves, is ground and an active ingredient is extracted by using water, an organic solvent or a mixture thereof. Examples of the organic solvent include lower alcohol (e.g. methanol, ethanol, or propanol), acetone, ethyl acetate, and ether (e.g. feedhyl ether). The extraction method is not specifically limited, and cold homogenizing extraction or reflux extraction can be used.

After extraction, if necessary, the resulting extract may be further extracted with water-saturated n-butanol or ethyl acetate and the resulting extract may be extracted again with water-containing ethanol. After extraction, the active ingredient is isolated by using adsorption chromatography, partition chromatography or ion-exchange chromatography and may be further purified by a conventional procedure.

Since the *Eucalyptus* extract in the present invention is obtained by the treatment for extraction form the plant of the genus *Eucalyptus*, it exhibits sufficient safety even if it is not sufficiently fractionated and purified. To the contrary, a crude drug effect with an undetected ingredient can be expected even if it is not purified.

The *Eucalyptus* extract in the present invention also contains gallic acid, ellagic acid, isoquercitrin, tellimagrandin I, tellimagrandin II, pedunculagin, 1,2,4-tri-0-galloyl-β-D-glucose, 1,2,3,6-tetra-0-galloyl-β-D-glucose, 1,2,4,6-tetra-0-galloyl-β-D-glucose, pentagalloylglucose, 1,3-di-0-galloyl-4,6-hexahydroxydiphenoyl-β-D-glucose, and 1,3-di-0-galloyl-4,6-hexahydroxydiphenoyl-α-D-glucose. It is presumed that one or more kinds of these substances are correlated to the activity of the *Eucalyptus* extract in the present invention.

The *Eucalyptus* extract is used in the form of drugs as an active ingredient for an anti-obestic action, an action of inhibiting lipid storage, an anti-lipemic action, an anti-arteriosclerotic action, an anti-thrombotic action, an action of inhibiting or reducing a concentration of triglyceride, or an action of inhibiting or reducing a concentration of cholesterol in blood, and is also used in the form of food products (food products and beverages), food additives, animal feeds, or additives for animal feeds. The amount the *Eucalyptus* extract to be administered or ingested to mammals is preferably within a range from 0.01 to 300 mg/kg weight/day. Even if the amount exceeds 300 mg/kg weight/day, safety is not impaired because the *Eucalyptus* extract is a natural product derived from the plant of the genus *Eucalyptus*.

To use the composition of the present invention in the form of drugs, the *Eucalyptus* extract as the active ingredient is formed into the form of a solid, semi-solid or liquid by adding a conventional biologically acceptable carrier or diluent. Specific form includes, for example, oral agents such as tablets, capsules, pills, granules, powders, emulsions, suspensions, syrups, and pellets; and parenteral agents such as injections, drops, and suppositories.

In case of forming into a preparation, there can be used carriers which are normally used according to dosage forms, for example, surfactants, excipients, binders, disintegrators, lubricants, stabilizers, buffers, and suspensions. Preferred examples thereof include solid carriers such as starch, lactose, mannitol, carboxymethylcellulose, corn starch, and inorganic salt; liquid carriers (diluents) such as distilled water, saline, aqueous glucose solution, alcohol (e.g. ethanol), propylene glycol, and polyethylene glycol; and oily carriers such as various animal and vegetable oils, white soft paraffin, paraffin, and wax.

Food products of the present invention are prepared by mixing the *Eucalyptus* extract with various components used in food products for the purpose of inhibiting or preventing obesity, lipid storage disease, hyperlipemia, arteriosclerosis and thrombosis, or for the purpose of inhibiting or reducing an amount of triglyceride or an amount of cholesterol in blood. The form of food products to be prepared may be any form of food products such as solid food product, cream-like or jam-like semi-solid food product, gel-like food product, and beverage. The *Eucalyptus* extract may be incorporated into food products as it is, or may be incorporated in the form of powder, granule, capsule, tablet, or liquid.

Various components (carriers or diluents) to be incorporated into food products, together with the *Eucalyptus* extract, are not specifically limited and there can be used any of various components which are conventionally used. These components are glucose, fructose, sucrose, maltose, sorbitol, stevioside, corn syrup, lactose, citric acid, tartaric acid, malic acid, succinic acid, lactic acid, L-ascorbic acid, dl-α-tocopherol, glycerin, propylene glycol, glycerin fatty ester, polyglycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors, and preservatives, and these components may be appropriately incorporated into food products according to the kinds of food products. In the present invention, use of the *Eucalyptus* extract in combination with sucrose (sugar) or fructose is particularly effective for inhibition, amelioration or prevention of obesity and lipid storage, and is also effective for inhibition of an increase or reduction of an amount of triglyceride or an amount of cholesterol in blood.

Specific examples of food products in the present invention include refreshing beverage, juice, coffee, tea, liqueur, milk, whey beverage, lactic acid beverage, candy, chewing gum, chocolate, gumdrop, yogurt, ice cream, and pudding. The amount of the *Eucalyptus* extract contained in food products is preferably within a range from 0.5 to 100 mg/g. Even if the *Eucalyptus* extract is incorporated in the amount which exceeds the above range, the safety and effect are not impaired.

The animal feed in the present invention is prepared by mixing the *Eucalyptus* extract with various components used in the animal feed for the purpose of inhibiting or preventing obesity, lipid storage, hyperlipemia, arteriosclerosis and thrombosis, or for the purpose of inhibiting or reducing an amount of triglyceride or an amount of cholesterol in blood. Specific examples of the animal feed include feed for livestock, and pet foods such as cat food and dog food. The amount of the *Eucalyptus* extract contained in the animal feed is preferably within a range from 0.5 to 100 mg/g. Even if the *Eucalyptus* extract is incorporated in the amount which exceeds the above range, the safety and effect are not impaired. In the present invention, use of the *Eucalyptus* extract in combination with sucrose (sugar) or fructose is particularly effective for inhibition, amelioration or prevention of obesity and lipid storage of animals, and is also effective for inhibition of an increase or reduction of an amount of triglyceride or an amount of cholesterol in blood.

Food additives or additives for animal feeds are added to food products for the purpose of inhibition, amelioration or prevention of obesity, lipid storage disease, hyperlipemia, arteriosclerosis and thrombosis, or for the purpose of inhibition or reduction of an amount of triglyceride or an amount of cholesterol in blood. The form of the food additive is not specifically limited and the *Eucalyptus* extract may be added to food products as it is, or the *Eucalyptus* extract may also be prepared in the form of a powder, capsule, syrup, gel, liquid or solid. Food products, to which the food additives of the present invention are added, are not specifically limited and include, for example, various cooked and processed food products. The amount may be almost the same as that in case of food products. The animal feed, to which the additives for animal feeds of the present invention are added, include animal feeds described above. The food additives may be added before, during or after cooking. Similarly, the animal feeds may also be added during or after preparation.

EXAMPLES

The following Reference Examples, Examples and Test Examples further illustrate the present invention in detail.

Reference Example

Dried leaves (500 g) of *Eucalyptus globulus* were refluxed with 4.5 kg of 33% ethanol for two hours. After the resulting solution was cooled to room temperature and filtrated, the filtrate was allowed to stand in a refrigerator overnight. After filtrate was further filtrated, the resulting filtrate was concentrated under reduced pressure and freeze-dried to obtain an unpurified *Eucalyptus* extract.

Test Example 1

Using the *Eucalyptus* extract obtained in the Reference Example, the following tests were conducted.

(1) Test for Measurement of Weight

Wistar rats (7 weeks-aged, male) were preliminarily bred for one week and then divided into two groups, each group consisting of four rats. Rats of each group were freely fed with a test feed (high sucrose feed) having the composition shown in Table 1 for eight weeks and a change in weight was examined. Breeding was conducted under the conditions of a temperature of $23 \pm 2°$ C., a humidity of $55 \pm 5\%$, and illumination for 12 hours/day.

TABLE 1

|  | Amount (g) | |
| --- | --- | --- |
| Components | Control group | Eucalyptus group |
| Casein | 170 | 170 |
| Sucrose | 700 | 700 |
| Vitamins | 10 | 10 |
| Minerals | 40 | 40 |
| Choline chloride | 2 | 2 |
| Methionine | 3 | 3 |
| Soybean oil | 30 | 30 |
| Crystalline cellulose | 45 | 35 |
| Eucalyptus extract | 0 | 10 |

The test results are shown in FIG. 1. FIG. 1 shows an average value of the weight of each group measured every other week. As is apparent from the drawing, regarding the

*Eucalyptus* group to which the *Eucalyptus* extract obtained in Reference Example was administered, an increase in weight is inhibited as compared with the control group.

(2) Test for Measurement of Lipid Storage Amount

Figure 2:
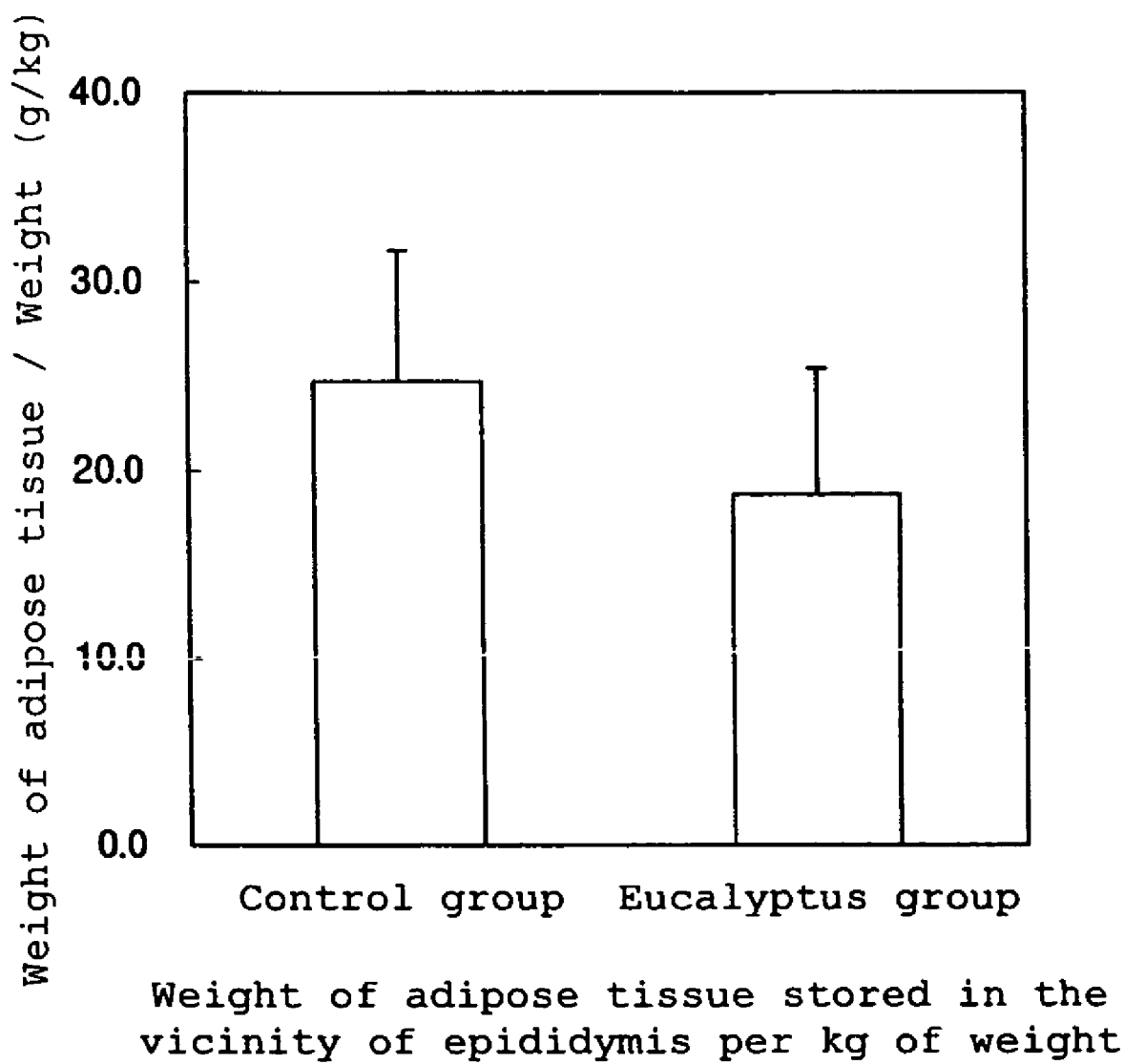
FIG. 2 is a graph showing an action of inhibiting lipid storage in Test Example 1.

After the completion of the breeding in the above test (1), the epididymis was removed and the weight of the adipose tissue stored in the vicinity of the epididymis was measured. Whereby, a large amount of visceral lipid can be presumed. The results are shown in FIG. 2. FIG. 2 shows the weight of adipose tissue stored in a vicinity of the epididymis per kg of weight with respect to the control group and the *Eucalyptus* group. As is apparent from FIG. 2, visceral lipid storage in the *Eucalyptus* group was inhibited as compared with the control group. As is apparent from the results, administration of the *Eucalyptus* extract is effective for preventing obesity and inhibiting an increase in weight.

(3) Test for Measurement of Amount of Triglyceride in the Liver

Figure 3:
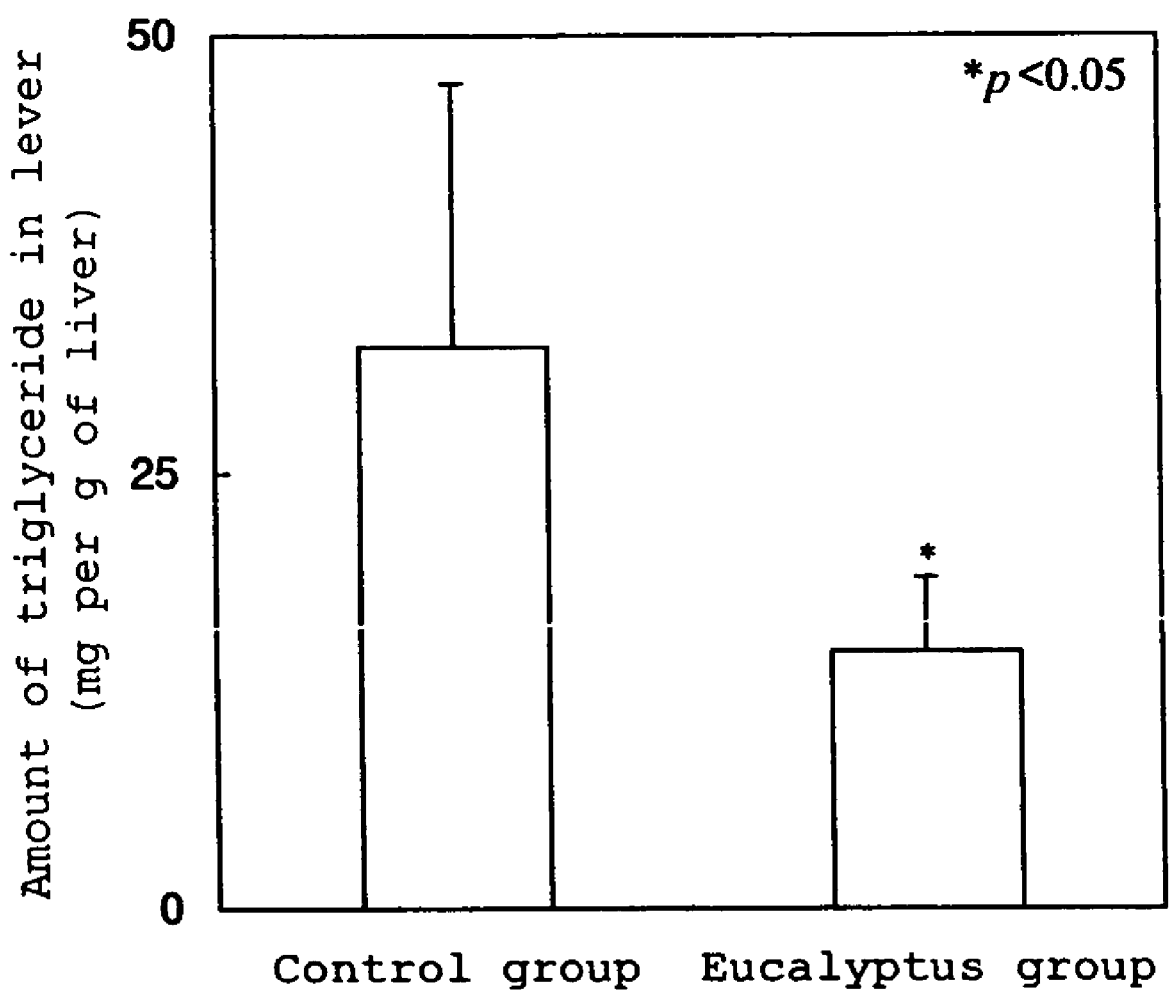
FIG. 3 is a graph showing an action of inhibiting triglyceride storage in the liver in Test Example 1.

After the completion of the breeding in the above test (1), a liver was removed. The liver was treated according to a conventional procedure, and then the amount of triglyceride in the liver was measured by "Triglyceride G-Test Wako" manufactured by Wako Pure Chemical industries, Ltd. The results are shown in FIG. 3. As is apparent from the drawing, triglyceride storage in the liver in the *Eucalyptus* group was inhibited as compared with the control group. As is apparent from the results, administration of the *Eucalyptus* extract has already exhibited an action of inhibiting lipid storage at an early stage (treatment in the liver) after injecting carbohydrate, and that administration of the *Eucalyptus* extract is effective for inhibition, amelioration or prevention of fatty liver and cirrhosis.

(4) Test for Measurement of Amount of Triglyceride and Cholesterol in Blood

After the completion of the breeding in the above test (1), blood was collected from the heart and treated according to a conventional procedure. The amount of triglyceride in blood was measured in the same manner as in the above test (3) and the amount of cholesterol in blood was also measured by "Cholesterol C-Test Wako" manufactured by Wako Pure Chemical industries, Ltd. The results are shown in FIG. 4 and FIG. 5.

Figure 4:
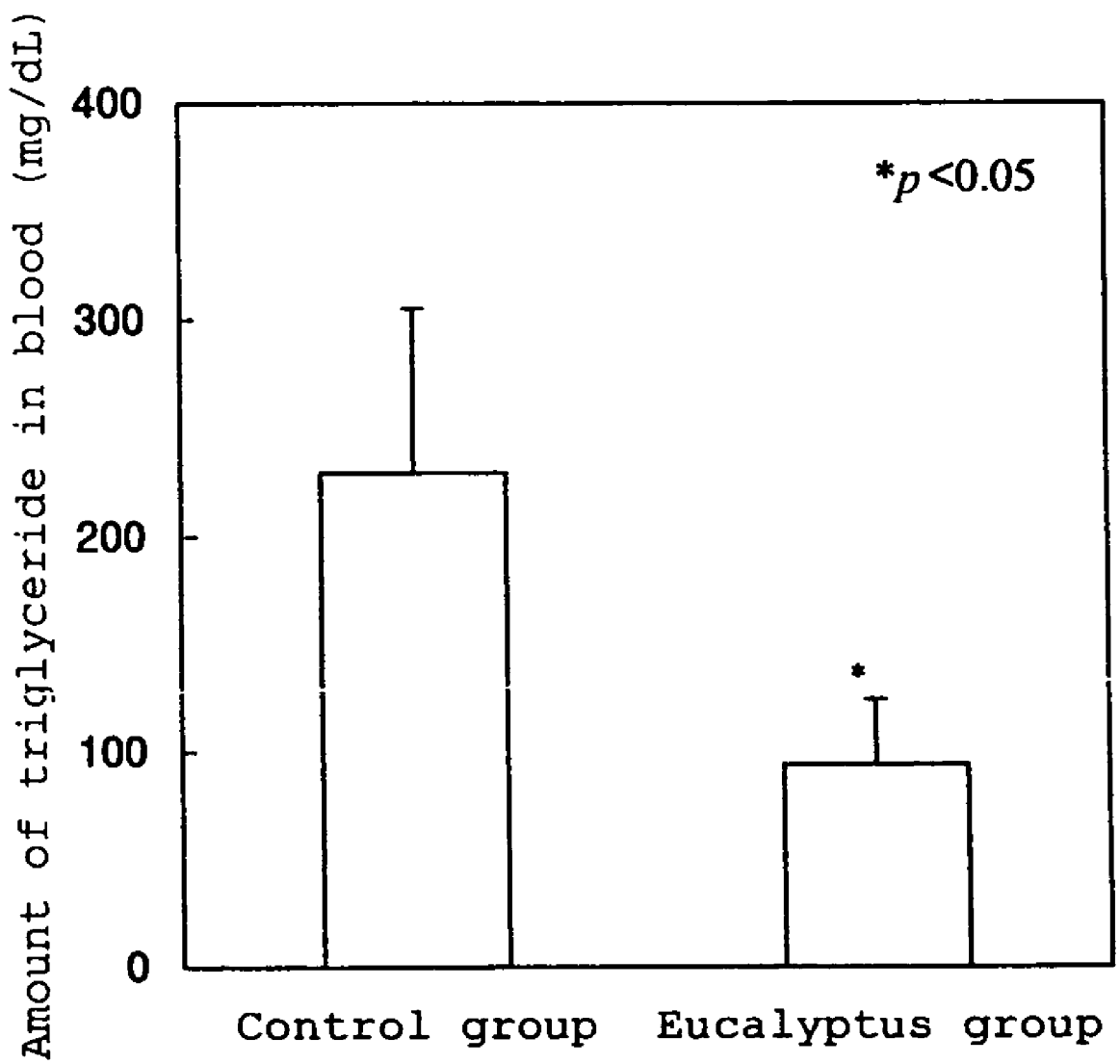
FIG. 4 is a graph showing an action of reducing an amount of triglyceride in blood in Test Example 1.
Figure 5:
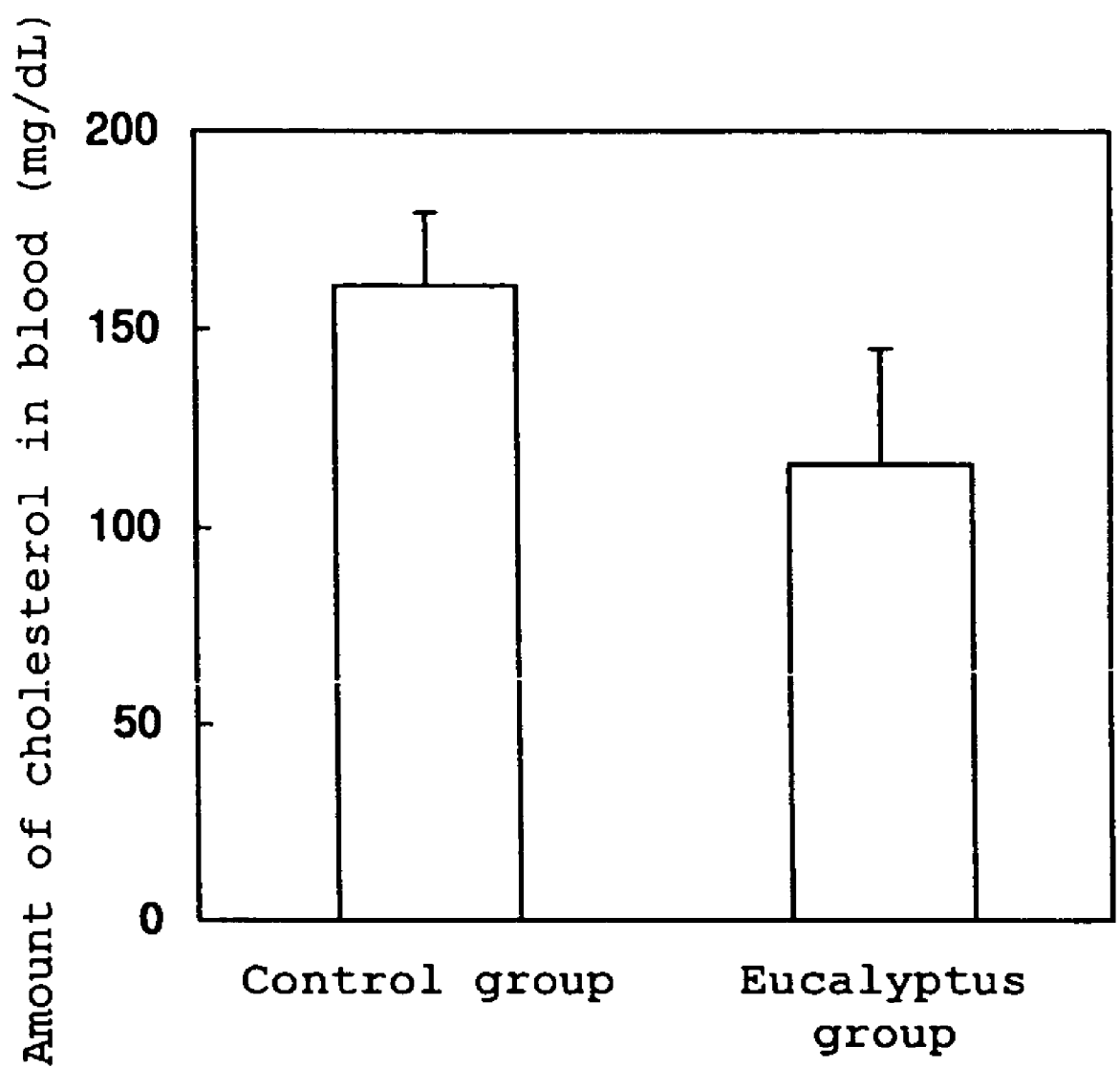
FIG. 5 is a graph showing an action of reducing an amount of cholesterol in blood in Test Example 1.
Figure 6:
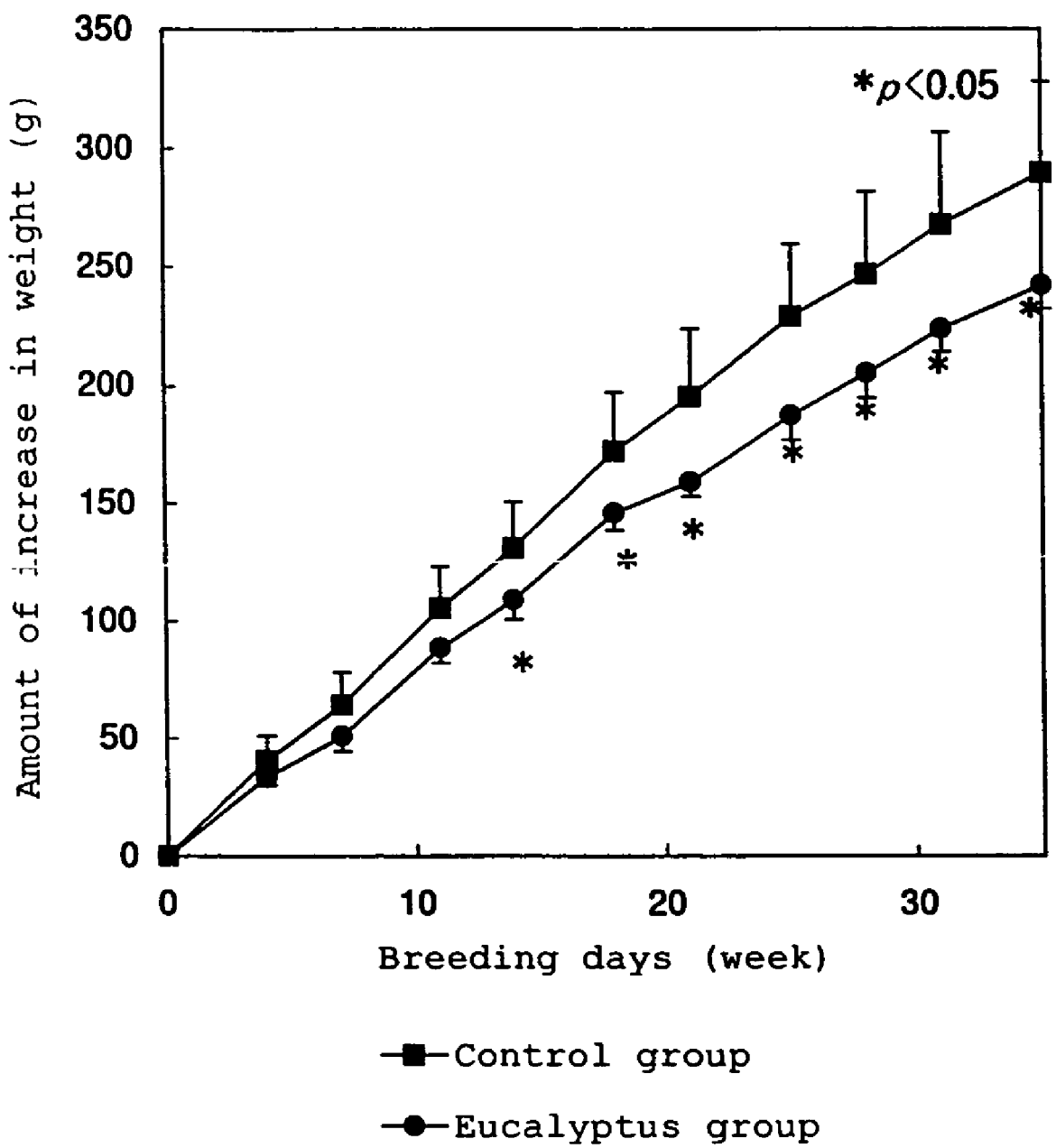
FIG. 6 is a graph showing an action of inhibiting an increase in weight in Test Example 2.
Figure 7:
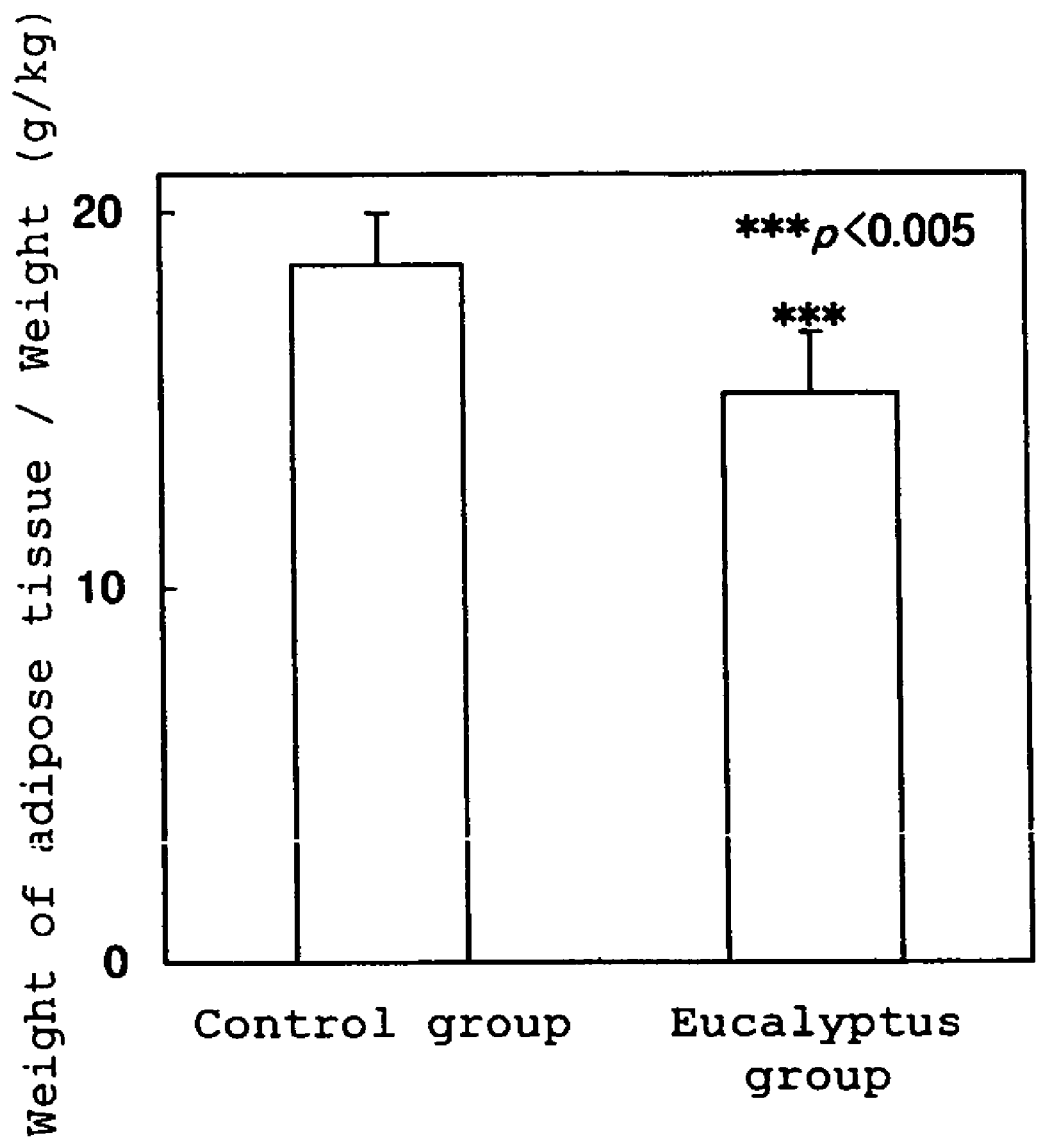
FIG. 7 is a graph showing an action of inhibiting lipid storage in Test Example 2.
Figure 8:
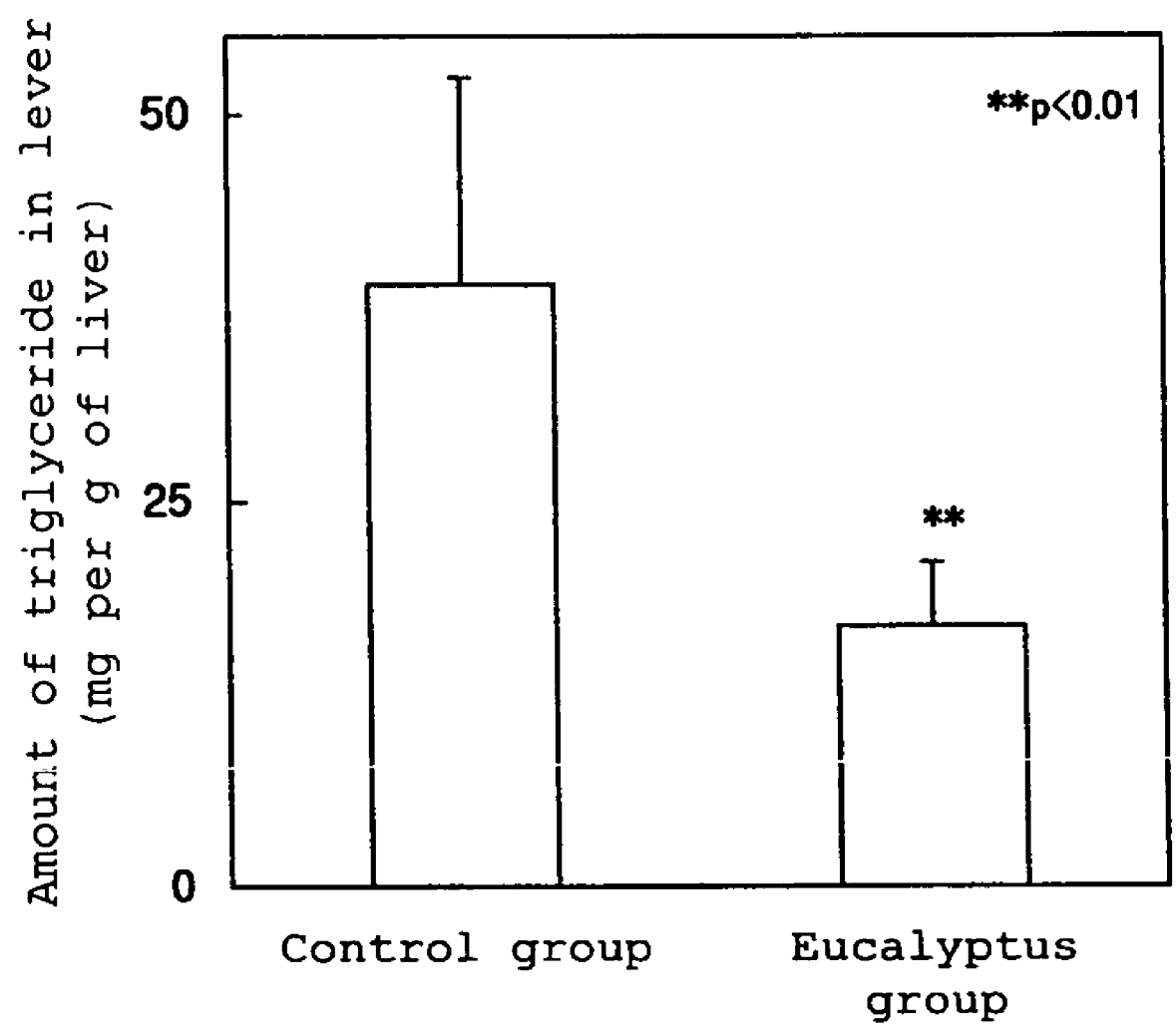
FIG. 8 is a graph showing an action of inhibiting triglyceride storage in the liver in Test Example 2.
Figure 9:
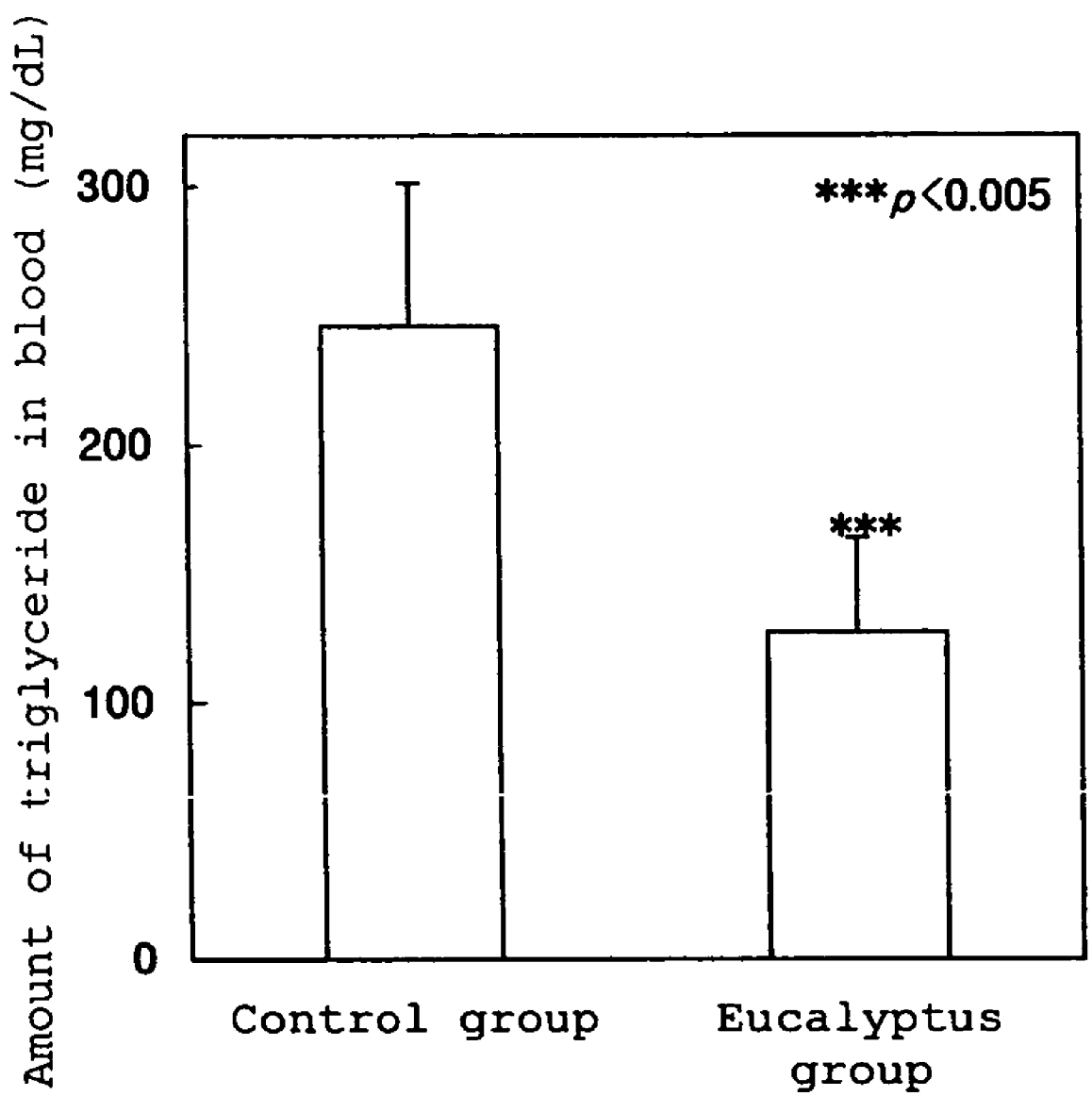
FIG. 9 is a graph showing an action of reducing an amount of triglyceride in blood in Test Example 2.
Figure 10:
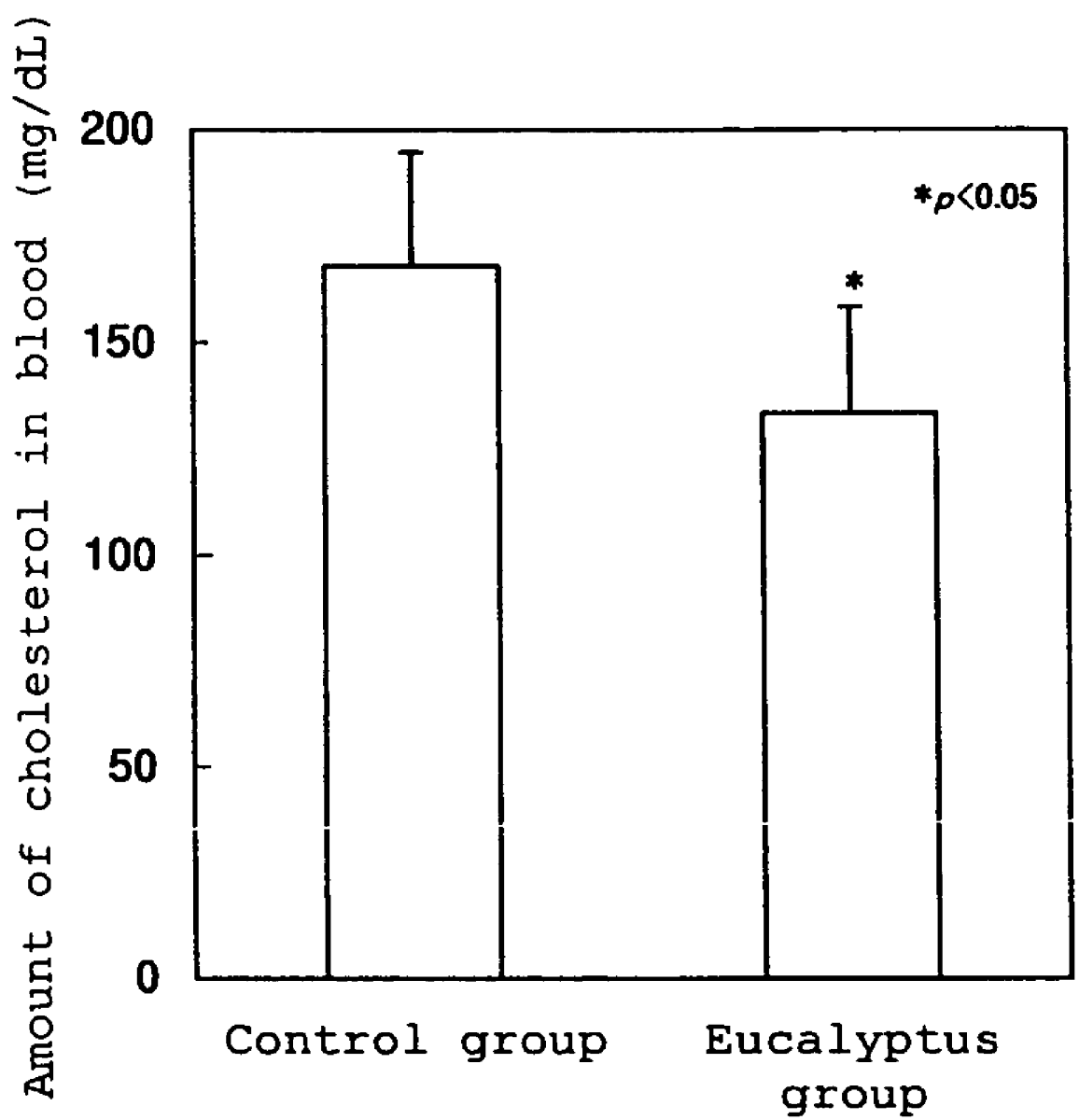
FIG. 10 is a graph showing an action of reducing an amount of cholesterol in blood in Test Example 2.

As is apparent from FIG. 4, the amount of triglyceride in blood in the *Eucalyptus* group was reduced as compared with the control group. As is apparent from FIG. 5, the amount of cholesterol in blood in the *Eucalyptus* group was reduced as compared with the control group. As is apparent from results, administration of the *Eucalyptus* extract is effective for inhibition, amelioration or prevention of diseases caused by a large amount of triglyceride in blood or cholesterol in blood, for example, arteriosclerosis, hypercholesterolemia, thrombosis, and hyperlipemia and the like.

Test Example 2

The test was conducted in the same manner as in Test Example 1, except that five weeks-aged Wistar rats (male) were divided into two groups, each consisting of seven rats, and rats of each group were freely fed with a test feed shown in Table 1 for 35 days. The results are shown in FIG. 6 to FIG. 10. As is also apparent from this Test Example, administration of the *Eucalyptus* extract is effective for inhibition, amelioration or prevention of obesity.

Example 1

Tablets 150 g of the *Eucalyptus* extract obtained in Reference Example was mixed with 150 g of lactose and 5 g of magnesium stearate, and then the mixture was compressed by a tablet machine to obtain tablets.

Example 2

Chocolate

Using the unpurified *Eucalyptus* extract obtained in the Reference Example, a chocolate was prepared according to the following formulation.

| (Components) | (Amount) |
| --- | --- |
| Cacao mass | 15.0 g |
| Sugar (sucrose) | 40.0 g |
| Whole milk powder | 25.0 g |
| Cocoa butter | 20.0 g |
| Eucalyptus extract | 1.0 g |
| Lecithin | 0.5 g |
| Flavor | 0.05 g |

Example 3

Cookie

Using the unpurified *Eucalyptus* extract obtained in the Reference Example, a cookie was prepared according to the following formulation.

| (Components) | (Amount) |
| --- | --- |
| Wheat flour | 100.0 g |
| Shortening | 20.0 g |
| Butter | 10.0 g |
| Sugar (sucrose) | 30.0 g |
| Egg | 4.0 g |
| Salt | 0.3 g |
| Eucalyptus extract | 0.5 g |
| Baking powder | 0.5 g |
| Flavor | 0.2 g |

Example 4

Candy

Using the unpurified *Eucalyptus* extract obtained in the Reference Example, a candy was prepared according to the following formulation.

| (Components) | (Amount) |
| --- | --- |
| Sugar (sucrose) | 50.0 g |
| Thick malt syrup | 50.0 g |
| Eucalyptus extract | 0.5 g |

-continued

| (Components) | (Amount) |
|---|---|
| Citric acid | 0.3 g |
| Flavor | 0.2 g |
| Pigment | q.s. |

Example 5

Dog Food

Using the unpurified *Eucalyptus* extract obtained in the Reference Example, a dog food was prepared according to the following formulation.

| (Components) | (Amount) |
|---|---|
| Meat meal | 45.6 g |
| Chicken extract | 6 g |

-continued

| (Components) | (Amount) |
|---|---|
| Vegetable fat and oil | 6 g |
| Carbohydrate | 44.4 g |
| Ash | q.s. |
| Vitamins | q.s. |
| Eucalyptus extract | 2.4 g |
| Water | 12 g |

What is claimed is:

1. A method of inhibiting visceral lipid storage, which comprises administering a composition comprising:
   (1) a biologically effective amount of an extract of a plant of the genus *Eucalyptus* as the active ingredient wherein the extract is obtained by grinding raw material of an *Eucalyptus* plant; and extracting the active ingredient from the ground raw material using a mixture of water and ethanol to obtain a resultant extract, and
   (2) a biologically acceptable carrier or diluent.

* * * * *